US012747423B2

(12) United States Patent
Kim et al.

(10) Patent No.: US 12,747,423 B2
(45) Date of Patent: Sep. 29, 2026

(54) CELL CULTURE MEDIUM FOR CULTURING EXTRACELLULAR VESICLES AT HIGH CONCENTRATION AND METHOD FOR PREPARING CONDITIONED MEDIUM CONTAINING HIGH CONCENTRATION OF EXTRACELLULAR VESICLES USING CELL CULTURE MEDIUM

(71) Applicant: BIOSOLUTION CO., LTD., Seoul (KR)

(72) Inventors: Jun Ho Kim, Seoul (KR); Ga Eun You, Seoul (KR); Jung Sun Lee, Seoul (KR); Song Sun Chang, Seoul (KR)

(73) Assignee: BIOSOLUTION CO., LTD., Seoul (KR)

( * ) Notice: Subject to any disclaimer, the term of this patent is extended or adjusted under 35 U.S.C. 154(b) by 1194 days.

(21) Appl. No.: 17/258,844

(22) PCT Filed: Mar. 5, 2020

(86) PCT No.: PCT/KR2020/003126
§ 371 (c)(1),
(2) Date: Jan. 8, 2021

(87) PCT Pub. No.: WO2020/230990
PCT Pub. Date: Nov. 19, 2020

(65) Prior Publication Data
US 2021/0269766 A1 Sep. 2, 2021

(30) Foreign Application Priority Data
May 10, 2019 (KR) ........................ 10-2019-0055184

(51) Int. Cl.
*C12N 5/00* (2006.01)
*C12N 5/0775* (2010.01)

(52) U.S. Cl.
CPC ......... *C12N 5/0018* (2013.01); *C12N 5/0662* (2013.01); *C12N 2500/14* (2013.01); *C12N 2500/24* (2013.01)

(58) Field of Classification Search
None
See application file for complete search history.

(56) References Cited

U.S. PATENT DOCUMENTS

2019/0015452 A1* 1/2019 Nishida .................. A61K 35/12

FOREIGN PATENT DOCUMENTS

| | | | |
|---|---|---|---|
| JP | S59-166079 A | 9/1984 |
| JP | 2015-500826 A | 1/2015 |
| JP | 2018-531979 A | 11/2018 |
| JP | 6448826 B1 | 1/2019 |
| KR | 10-2005-0041178 A | 5/2005 |
| KR | 10-2016-0125352 A | 10/2016 |
| KR | 10-2019-0026285 A | 3/2019 |
| WO | WO-2017/076924 A1 | 5/2017 |
| WO | WO-2019/132831 A2 | 7/2019 |

OTHER PUBLICATIONS

Zonneveld, Marijke I., et al. "Recovery of extracellular vesicles from human breast milk is influenced by sample collection and vesicle isolation procedures." Journal of extracellular vesicles 3.1 (2014): 24215. (Year: 2014).*
Dry, Helen, et al. "Effect of calcium on the proliferation kinetics of synovium-derived mesenchymal stromal cells." Cytotherapy 15.7 (2013): 805-819. (Year: 2013).*
InVitra, Lacromin Recombinant Human Lactoferrin (Holo), Guidelines for Use, Feb. 2016. (Year: 2016).*
Baker, et al. (2002) "Lactoferrin and transferrin: Functional variations on a common structural framework.", *Biochem Cell Biol.*, 80(1):27-34.
Cha, et al. (2018) "Efficient scalable production of therapeutic microvesicles derived from human mesenchymal stem cells.", *Sci Rep.*, 8(1) 1171, pp. 1-16.
EL Andaloussi, et al. (2013) "Extracellular vesicles: biology and emerging therapeutic opportunities.", *Nat Rev Drug Discov.*, 12(5):347-357.
Hugel, et al. (2005) "Membrane Microparticles: Two Sides of the Coin.", Physiology 20:22-27. doi:10.1152/physiol.00029.2004.
Konoshenko, et al. (2018) "Isolation of Extracellular Vesicles: General Methodologies and Latest Trends.", *BioMed Research International*, vol. 2018, Article ID 8545347, 27 pages.
Lener, et al. (2015) "Applying extracellular vesicles based therapeutics in clinical trials—an ISEV position paper.", *Journal of Extracellular Vesicles*, 4:1, 30087, DOI: 10.3402/jev.v4.30087.
N.W. Seidler, (2013) *GAPDH: Biological Properties and Diversity*, Advances in Experimental Medicine and Biology 985, DOI 10.1007/978-94-007-4716-6_3, Chapter 3, Compartmentation of GAPDH, pp. 61-101.
Savina, et al. (2003) "Exosome Release Is Regulated by a Calcium-dependent Mechanism in K562 Cells*.", *J Biol Chem.*, 278(22):20083-20090.
International Search Report from corresponding PCT Application No. PCT/KR2020/003126, dated Jun. 15, 2020, with English translation.

* cited by examiner

*Primary Examiner* — Anoop K Singh
*Assistant Examiner* — Constantina E Stavrou
(74) *Attorney, Agent, or Firm* — Harness, Dickey & Pierce, P.L.C.

(57) ABSTRACT

The present invention relates to: a cell culture medium for culturing extracellular vesicles at high concentration, the medium comprising lactoferrin; a method for preparing a conditioned medium containing a high concentration of extracellular vesicles, the method comprising culturing cells in the cell culture medium; and use of lactoferrin in preparing a conditioned medium containing a high concentration of extracellular vesicles.

5 Claims, 6 Drawing Sheets

CELL CULTURE MEDIUM FOR CULTURING EXTRACELLULAR VESICLES AT HIGH CONCENTRATION AND METHOD FOR PREPARING CONDITIONED MEDIUM CONTAINING HIGH CONCENTRATION OF EXTRACELLULAR VESICLES USING CELL CULTURE MEDIUM

CROSS-REFERENCE TO RELATED APPLICATIONS

This application is a national phase application of PCT Application No. PCT/KR2020/003126, filed on Mar. 5, 2020, which claims benefit of Korean Patent Application No. 10-2019-0055184, filed May 10, 2019. The entire disclosure of the applications identified in this paragraph are incorporated herein by references.

FIELD

The present invention relates to a cell culture medium for culturing extracellular vesicles at a high concentration, comprising lactoferrin; a method for preparing a conditioned medium containing extracellular vesicles at a high concentration comprising culturing cells in the cell culture medium; and a use of lactoferrin for use in preparing a conditioned medium containing extracellular vesicles at a high concentration.

BACKGROUND

Among cell secreted substances, "extracellular vesicles" have recently attracted attention. Extracellular vesicles are small and spherical objects with a size of 30 nm to 2 μm (2,000 nm) as cell-mimicking carriers released from cells. Extracellular vesicles refer to various vesicles released from cells, and the main classifications are "exosomes" and "microvesicles." The types of extracellular vesicles are named differently by scholars according to function and origin of vesicles, and are called by various names such as Ectosomes, Microparticles, Tolerosomes, Prostatosomes, Cardiosomes, Vexosomes etc., but in the end, it is reported that it is appropriate to be named as exosomes derived from endosome intraluminal vesicle and microvesicles derived from plasma membrane according to the principle of generation (Nat Rev Drug Discov. 2013 May; 12(5):347-57). The main feature thereof is that they are enclosed in a cell-derived lipid bilayer to have a membrane protein and contain a cell regulatory protein inside.

One of the reasons that the field of extracellular vesicles has been activated recently is that it is difficult to separate them from other secreted proteins due to the small size of the extracellular vesicles, and to confirm their effect due to the low content of extracellular vesicles in the culture medium. Currently, a technology for separating extracellular vesicles has been secured (Biomed Res Int. 2018 Jan. 30; 2018: 8545347), its effectiveness has been confirmed, and clinical trials are in progress (J Extracell Vesicles. (2015)31; 4:30087).

However, it is difficult to confirm the specific effect of extracellular vesicles only in a general conditioned medium obtained by culturing cells with a general cell culture medium for extracellular vesicles having a low content of cell secreted substances, and even if extracellular vesicles are separated from the conditioned medium and utilized, there is a limitation due to the lack of an absolute amount of extracellular vesicles.

Currently, research is underway to increase the content of extracellular vesicles in the conditioned medium by allowing cells to excrete more extracellular vesicles. Fundamentally, a method of increasing the total concentration of secretions secreted by the cells by growing many cells in the same space is used (Sci Rep. 2018 Jan. 19; 8(1):1171). However, since this method is not a method of increasing the ratio of extracellular vesicles alone, it is not a method to solve the cause, and this method has a limitation in increasing the secretion amount and has a problem in terms of cost.

Therefore, there is a need for a method for cells to specifically excrete extracellular vesicles. That is, if only the extracellular vesicles excreted from the cells are specifically increased, the content of extracellular vesicles in the culture medium will increase and the absolute amount will also increase.

SUMMARY

Technical Problem

The key to the development of technology to improve productive capacity of extracellular vesicles excreted per single cell is that the cell culture medium does not contain human toxic substances and does not require high cost/inefficient work. In addition, the substances used should not negatively affect the function of extracellular vesicles, and furthermore, it will be a more effective method if the substances used can improve the function of the extracellular vesicles.

Accordingly, it is a technical problem of the present invention to develop a cell culture medium for culturing extracellular vesicles at a high concentration which meet all of the above conditions, and to provide a method for preparing a medium containing the extracellular vesicles at a high concentration.

Solution to Problem

The present inventors have endeavored to solve the above problems, and as a result, found that a protein called lactoferrin satisfies all of the above conditions and is very effective in increasing the amount of extracellular vesicles produced. Furthermore, the present inventors have found that when extra calcium is added to lactoferrin, the productive capacity of extracellular vesicles by lactoferrin can be further maximized, and the present invention has been completed.

The present inventors have confirmed that a conditioned medium containing a high concentration of exosomes is formed spontaneously based on the effect of increasing the excreted amount of extracellular vesicles produced per single cell by lactoferrin. In addition, it was found that it was possible to prepare a cell culture medium to which lactoferrin was added, and to make a high concentration conditioned medium.

Accordingly, the present invention provides a cell culture medium for culturing extracellular vesicles at a high concentration comprising lactoferrin.

In addition, the present invention provides a method for preparing a conditioned medium containing a high concentration of extracellular vesicles comprising culturing cells in the cell culture medium.

In addition, the present invention provides the use of lactoferrin for use in preparing a conditioned medium containing an extracellular vesicle at a high concentration.

Effects of Invention

The cell culture medium capable of culturing the extracellular vesicles at a high concentration comprising lactoferrin of the present invention is safe since it uses lactoferrin, which is not toxic to the human body, and can efficiently increase the amount of extracellular vesicles produced.

DETAILED DESCRIPTION

Figure 1:
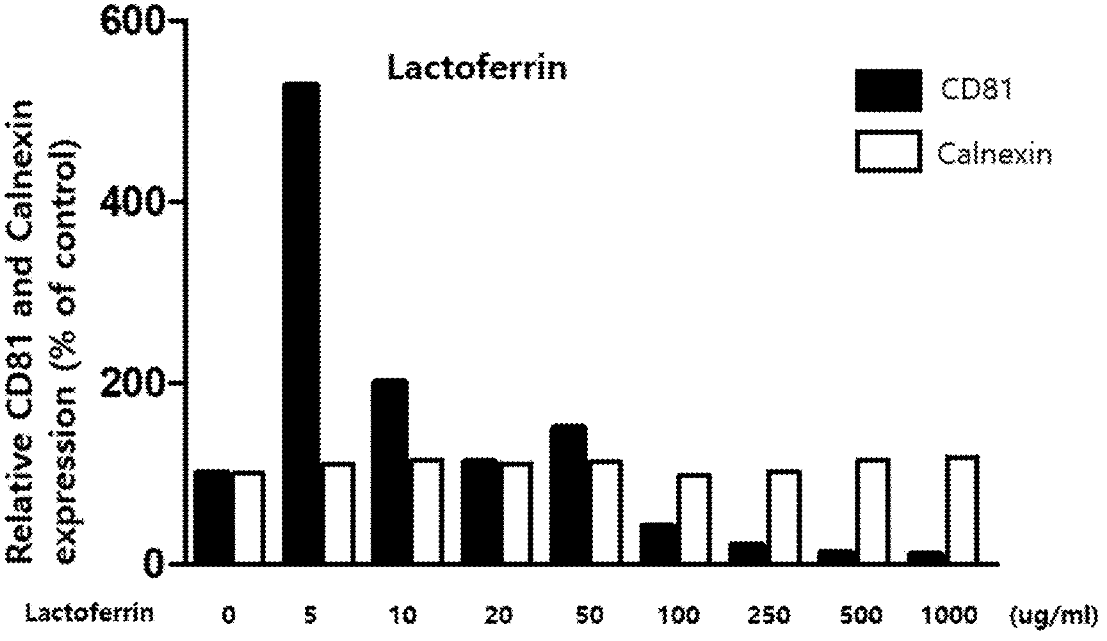
FIG. 1 is an ELISA result of confirming the generation rate of extracellular vesicles in the conditioned medium by CD81 and the generation rate of apoptotic vesicles by calnexin when lactoferrin is combined in the basal media by concentration.

The present inventors have found that lactoferrin is effective in increasing the amount of extracellular vesicles produced by binding to cell receptors. Furthermore, the present inventors produced a cell culture medium for the production of extracellular vesicles that comprise lactoferrin essentially and optionally further contain calcium in order to increase the calcium delivery ability of lactoferrin, and have confirmed that when the culture medium is used in cell culture, the productive capacity of extracellular vesicles excreted by cells was rapidly increased.

The cell culture medium of the present invention and the cell culture method using the same are safe in that they use a combination of lactoferrin protein, which is not toxic to humans, and calcium ions, and can efficiently increase the amount of extracellular vesicles produced.

The present invention relates to a cell culture medium for culturing extracellular vesicles at a high concentration comprising lactoferrin.

In addition, the present invention relates to a method for preparing a conditioned medium containing extracellular vesicles at a high concentration comprising culturing cells in the cell culture medium.

Furthermore, the present invention relates to a use of lactoferrin for use in preparing a conditioned medium containing extracellular vesicles at a high concentration.

The term "extracellular vesicle" as used herein refers to various vesicles excreted from cells and is meant to include "exosome" and "microvesicle." Furthermore, the term "extracellular vesicle" is also used in the meaning of including ectosomes, microparticles, talerosomes, prostatosomes, cardiosomes and bexosomes.

The term "cell culture medium" as used herein refers to a medium before culturing cells and "conditioned medium" refers to a culture medium (medium) obtained after culturing cells.

In one embodiment, lactoferrin may be added to the cell culture medium at a concentration of 0.1 μg/ml to 1 mg/ml. In one embodiment, lactoferrin may be selected from the group consisting of holo-lactoferrin, apo-lactoferin and pis-lactoferrin. Specifically, said lactoferrin may be obtained by synthesis or extraction, and includes both human or non-human animal origins.

In one embodiment, the number of extracellular vesicles in the conditioned medium obtained by the method for preparing a conditioned medium of the present invention may range from $1.0\times10^{8}$/ml to $1.0\times10^{11}$/ml, and specifically may range from $1.0\times10^{9}$/ml to $1.0\times10^{11}$/ml.

According to one embodiment of the present invention, the cell culture medium of the present invention may additionally include calcium. The present inventors have confirmed that the productive capacity of extracellular vesicles by lactoferrin can be further maximized by controlling the concentration of calcium combined with lactoferrin. In one embodiment, said calcium may be added in the form of calcium ions ($Ca^{2+}$), and the source of calcium ions includes all salts capable of supplying calcium ions.

In one embodiment, calcium may be added to the cell culture medium at a concentration of 0.2 μM to 10 mM.

In one embodiment, the cell culture medium of the present invention may be not set at a specific time point during cell culture and is repeatedly used.

According to one embodiment of the present invention, the method for preparing the cell culture medium or the conditioned medium of the present invention may be combined with a medium used for culturing existing cells—for example, a medium containing a serum replacement. In one embodiment, the method for preparing the cell culture medium and the conditioned medium of the present invention may additionally include adding one or more substances selected from the group consisting of the basal media, serum replacements and serums. In one embodiment, the cell culture medium of the present invention may additionally include one or more substances selected from the group consisting of the basal media, a serum replacement and a serum. The term "serum replacement" refers to the composition which replaces serum for preparing a serum-free medium.

According to one embodiment of the present invention, the combination of lactoferrin, calcium ions and serum replacements can maximize the productive capacity of extracellular vesicles of the cells.

Transferrin, which is included in serum replacements, is known to increase the production of extracellular vesicles by increasing the concentration of intracellular calcium (J Biol Chem. 2003 May 30; 278(22):20083-90). Lactoferrin is a family of transferrins, and the sequence thereof is about 60% identical to transferrin. Therefore, lactoferrin is similar to transferrin in its structural features and representative functional characteristics such as the ability to bind iron ions.

However, since lactoferrin has a different isoelectric point from transferrin, the ionic binding ability is different due to the different extent of surface positive charge, and the receptors to which families bind are also different (Biochem Cell Biol. 2002; 80(1):27-34). In the Examples to be described later, the effects of lactoferrin and transferrin showing these differences on the amount of extracellular vesicles produced were confirmed using an enzyme-linked immunosorbent assay (ELISA), and the production extent of CD81, which is the extracellular vesicle marker, and apoptotic vesicles were observed with calnexin, which is a marker factor. As a result, it was observed that the extracellular vesicle-production effect of transferrin was not higher than that of lactoferrin. It was observed that lactoferrin significantly increased intracellular calcium concentration and increased the amount of extracellular vesicles produced by surpassing serum replacements based on specific differences in ion binding and the ability to bind to cell receptors.

As confirmed in the Examples to be described later, the principle that the cell culture medium to which lactoferrin is added according to the present invention increases the number of extracellular vesicles is not a result of the increase of cell proliferation or death substances, but due to the increase in the capacity of cells to directly produce extracellular vesicles by increasing the concentration of intracellular calcium (PHYSIOLOGY 20: 22-27, 2005; 10.1152). In addition, the process by which lactoferrin binds to GAPDH (glyceraldehyde 3-phosphate dehydrogenase), which is the cell receptor, and moves inside the cell is a common phenomenon that is applied to all cells of animals, including humans (GAPDH: Biological Properties and Diversity, ISBN 978-94.-007-4716-6). Therefore, preparing the conditioned medium containing high concentration exosomes with a cell culture medium to which lactoferrin is added is a universal method applicable to all kinds of cells of animals including humans.

In one embodiment, the cells used in the method for preparing the cell culture medium and the conditioned medium of the present invention may be all kinds of cells derived from humans or animals.

The conditioned medium containing extracellular vesicles at a high concentration can be easily prepared through the method for preparing the conditioned medium of the present invention. Furthermore, by using the cell culture medium of the present invention, the cell culture medium containing an extracellular vesicle at a high concentration can be easily prepared.

The term "high concentration of extracellular vesicles" as used herein refers to a case in which the number of extracellular vesicles in the culture medium obtained by culturing cells is in the range of at least $1.0\times10^{8}$/ml to $1.0\times10^{11}$/ml.

The conditioned medium or cell culture medium obtained by this method contains extracellular vesicles at a high concentration, and thus can be widely and conveniently used as a raw material for cosmetics and therapeutic agents.

Hereinafter, the Examples are intend to be described in more detail about the configurations and effects of the present invention. However, the following examples are only intended to illustrate the invention, and the scope of the present invention is not limited thereto.

EXAMPLES

Example 1: Increasing the Amount of Extracellular Vesicles Produced Using Lactoferrin Lactoferrin (LF) is a family of transferrin (TF), and the sequence thereof is about 60% identical to transferrin. Therefore, lactoferrin is similar to transferrin in its structural features and representative functional characteristics such as the ability to bind iron ions. On the other hand, since lactoferrin has a different isoelectric point from transferrin, the ionic binding ability is different due to the different extent of surface positive charge, and the receptors to which families bind are also different. The effects of lactoferrin and transferrin showing these differences on the amount of extracellular vesicles produced were confirmed using an enzyme-linked immunosorbent assay (ELISA), and the production extent of CD81, which is the extracellular vesicle marker, and apoptotic vesicle was observed with calnexin, which is a marker factor.

Specifically, human adipose-derived mesenchymal stem cells were cultured for 24 hours in a plate culture dish (48-well plate). After 24 hours, lactoferrin (Aspira Scientific, USA) or transferrin (Sigma, USA) was mixed with water so that the final concentration was 5, 10, 20, 50, 100, 250, 500 and 1000 μg/ml, and 25 μl of each was inoculated into the basic medium. The negative control was inoculated with 25 μl of water. After treatment, after incubation for 24 hours in a 37° C. incubator supplying 5% $CO_2$, each culture medium was obtained and centrifuged at 1,500 g for 10 minutes to remove dead cells.

CD81 and calnexin were measured using the CD81 ELISA kit (Mybiosource, USA) and calnexin ELISA kit (Mybiosource, USA), and the specific method is as follows. 100 μl each of the obtained culture medium and standard were added to a coated 96-well plate, and then reacted at 37° C. for 1 to 2 hours. Thereafter, the standard and the culture medium were removed, and the first antibody (detection antibody) was added to react at 37° C. After 1 hour, the mixture was washed three times with a wash buffer, and a second antibody (HRP antibody) was added to react, followed by washing again after 0.5-1 hour. Finally, a substrate and a stop buffer were added, and the absorbance was measured at 450 nm with an ELISA reader (Molecular Devices, USA), and the ratio calculated based on the negative control was shown in FIG. 1 (lactoferrin) and FIG. 2 (transferrin). Results for CD81 were represented by black bars, and results of calnexin were represented by white bars.

As shown in FIG. 1, it was confirmed that lactoferrin can increase the amount of extracellular vesicles produced which are excreted by cells at a specific concentration. It was confirmed that CD81, an extracellular vesicle marker, was increased by as little as 1.5 fold (in case of 50 μg/ml lactoferrin) and as much as 5 fold (in case of 5 μg/ml lactoferrin) as compared to the untreated group (0 μg/ml) at a lactoferrin concentration of 5 μg/ml, 10 μg/ml and 50 μg/ml. Relatively, calnexin, a marker of apoptosis, was not significantly different in lactoferrin concentrations. In conclusion, lactoferrin was identified as a protein that specifically increases the production of exosomes and microvesicles, which are two types of extracellular vesicles in the concentration range used.

Figure 2:
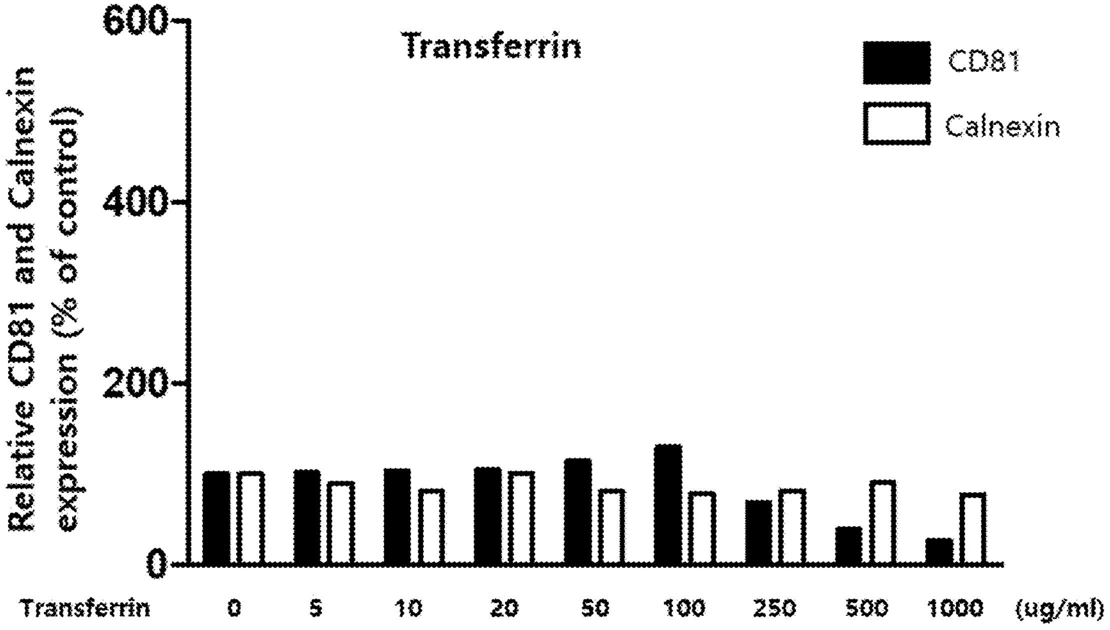
FIG. 2 is an ELISA result of confirming the generation rate of extracellular vesicles in the conditioned medium by CD81 and the generation rate of apoptotic vesicles by calnexin when transferrin is combined in the basal media by concentration.

On the other hand, transferrin under the same concentration condition showed no significant difference in change compared to the increase in CD81 of lactoferrin (FIG. 2). This confirms that lactoferrin is an effective substance specifically for increasing the production of extracellular vesicles that cells excrete.

Example 2: Increase of Intracellular Calcium Level by Lactoferrin/Calcium Composition Increasing the concentration of calcium in the cell is directly related to the increased production of extracellular vesicles. The increase of intracellular calcium symmetrically reverses the asymmetry of the cell membrane proteins and disrupts the membrane that maintains the balance (Physiology (Bethesda) 2005 February; 20:22-7). It is also known that an increase of the intracellular calcium concentration increases the production of intraluminal vesicles in the endosome.

Since serum replacements activate cell metabolism through many nutrients in addition to transferrin, it is advantageous to include serum replacements in the culture medium that produces extracellular vesicles. On the other hand, transferrin included in serum replacements is known to increase the production of extracellular vesicles by increasing the concentration of intracellular calcium (J Biol Chem. 2003 May 30; 278(22): 20083-90), but the extracellular vesicle-production effect of transferrin is not higher than that of lactoferrin, as confirmed from the results of Example 1 above.

On the other hand, the following experiment was designed because lactoferrin has the potential to significantly increase intracellular calcium concentration and further increase the production of extracellular vesicles by surpassing serum replacemnets based on specific differences in ion binding and the ability to bind to cell receptors.

In order to measure the intracellular calcium level according to the concentration of lactoferrin, a calcium colorimetric assay kit (Biovision, USA) was used. The calcium colorimetric measurement kit measures the concentration of calcium using the principle of measuring the color displayed by the reaction of 0-cresolphthalein and calcium.

Human adipose-derived mesenchymal stem cells were cultured for 4 days. After removing the culture medium and washing with a phosphate buffer solution, the cells were treated by mixing calcium and lactoferrin (Aspira Scientific, USA) at different concentrations (2, 5, 10, 25, 50 and 100 μg/ml) in a medium containing a serum replacement. Along with this, the experiment was performed with the group combining only the serum replacement+calcium, the group treated with only 10 μg/ml of lactoferrin, the group treated with only the serum replacement and the basal media group without any addition. After 48 hours, the cells were washed with a phosphate buffer solution, and they were separated from the culture dish with a 1× trypsin-EDTA (0.05% trypsin, 0.53 mM EDTA, Welgene, Korea) solution.

The number of cells in each group was measured with an automatic cell counter (nucleocounter NC-250, Chemometec, USA), and the same number of cells were dissolved in a calcium assay buffer (Biovision, USA). Subsequently, an experiment was conducted using the calcium colorimetric measurement kit. 50 μl of sample per well or quantitative calcium and 90 μl of chromogenic reagent (0-cresolphthalein), and 60 μl of calcium assay buffer were added to a 96-well plate and were reacted for 5 minutes by blocking the light. Subsequently, the absorbance was measured at 575 nm, and culturing mesenchymal stem cells in the basal media was set to 100% to show the relative increase.

Figure 3:
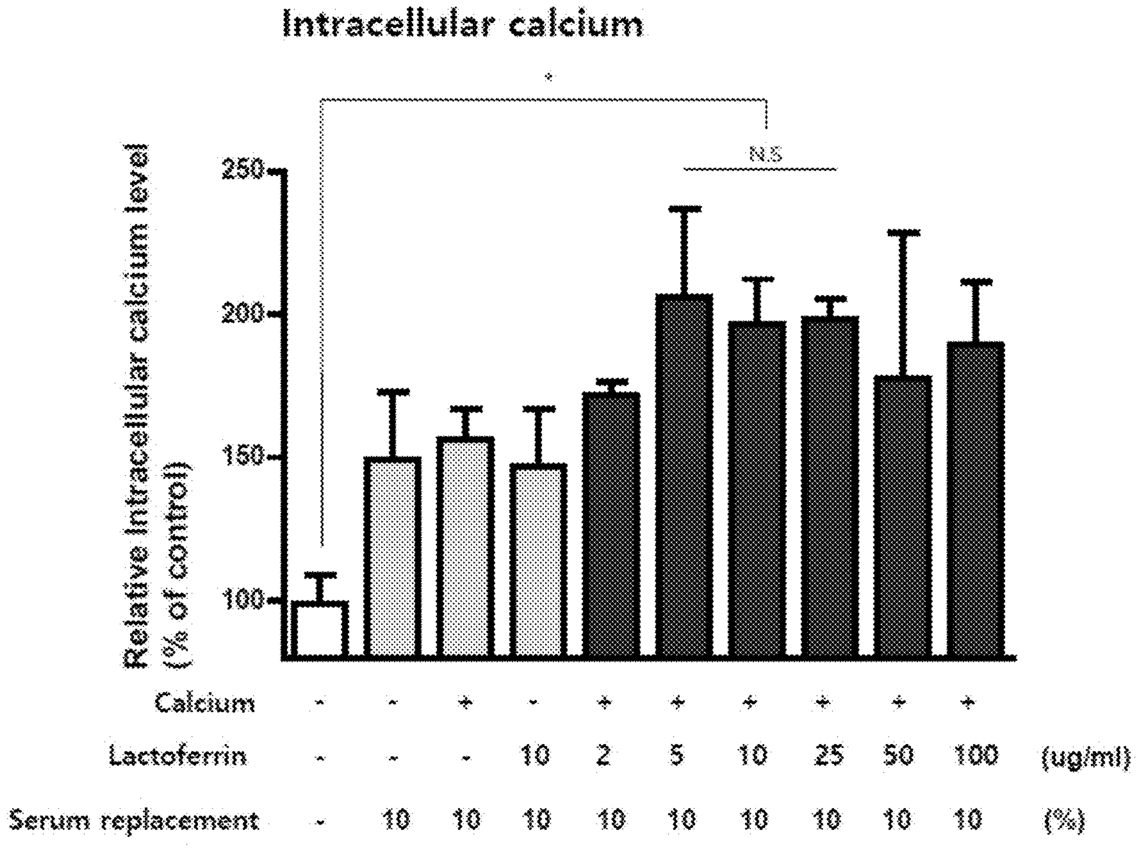
FIG. 3 is a result of confirming the change in the intracellular calcium concentration in the conditioned medium when a serum replacement, lactoferrin and calcium are combined in the basal media.

As shown in FIG. 3, it was confirmed that the lactoferrin/calcium composition was combined with a serum replacement to significantly increase the intracellular calcium concentration. When only the serum replacement was added to the basal media, it was confirmed that the calcium concentration of about 150% increased as expected. However, even when more calcium was supplied, the intracellular calcium concentration by the serum replacement did not increase any more (Tukey's test, $p>0.05$). On the other hand, when 2 μg/ml of lactoferrin was additionally supplied with calcium, the intracellular calcium concentration increased as compared with that of the serum replacement, and the highest intracellular calcium concentrations was shown at concentrations of 5 μg/ml, 10 μg/ml and 25 μg/ml. In general, it was confirmed that lactoferrin 5, 10 and 25 μg/ml and calcium composition could significantly increase the intracellular calcium concentration compared to the basal media (Tukey's test, $p<0.05$).

From the above results, it could be found that the lactoferrin/calcium composition increases the intracellular calcium concentration, and the composition has the potential to further increase the amount of extracellular vesicles produced in combination with a serum replacement. It was found that the range of cells to which lactoferrin is applicable can be applied not only to the adipose-derived mesenchymal stem cells used in the above experiment, but to all types of cells.

A one-way ANOVA was performed to confirm that there was a difference within the entire group, and the difference between individual means was analyzed using the Tukey's test. The statistical clarity between groups was plotted as *=($p<0.05$), N.S=($p>0.05$). The statistics were analyzed using Prism software version 5.

Example 3: Increase in Extracellular Vesicle Production by Lactoferrin/Calcium Composition Nanoparticle tracking analysis (NTA) was performed to observe the change in the number and size of extracellular vesicles in the culture medium according to the concentration of lactoferrin.

Human adipose-derived mesenchymal stem cells were cultured for 2 days. Lactoferrin concentrations of 5 μg/ml, 10 μg/ml and 50 μg/ml were combined with calcium and then combined with a serum replacement, mixed in the basal media, and replaced. In addition, the experiment was performed by comparing the group containing only the basal media (alpha-MEM) including the serum replacement and the group containing only the basal media. After 48 hours, the culture medium was collected, centrifuged at 1500 g for 10 minutes, and then the number and size of extracellular vesicles in the culture medium were measured with a nanoparticle tracking analysis (NTA, Nanosight NS300, Malvern, UK), and are shown in FIGS. 4 and 5.

Figure 4:
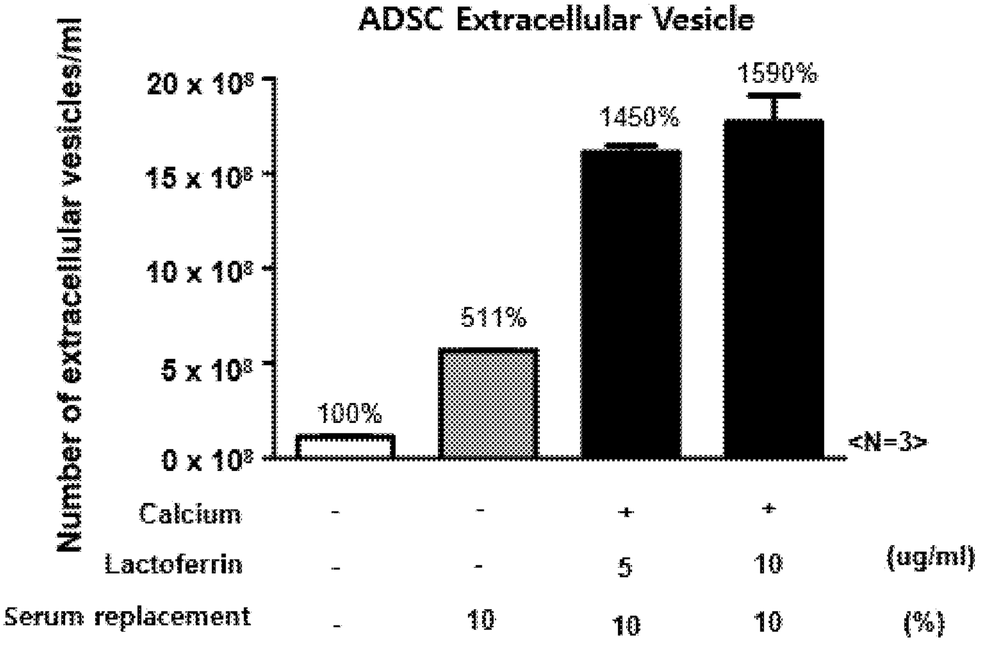
FIG. 4 is a result of measuring the number of extracellular vesicles generated in a conditioned medium with a nanoparticle tracking analyzer when a serum replacement, lactoferrin, and calcium are combined in the basal media.

FIG. 4 is a graph showing the number of extracellular vesicles included per ml of the culture medium, and the relative number of extracellular vesicles was calculated based on the basal media (100%) and shown at the top of each graph. As shown in FIG. 4, as a result of checking the number of extracellular vesicles included in the medium with a nanoparticle measuring device, the average extracellular vesicles were found to be $1.1\times10^8$ cells/ml in the basal media. The serum replacement treatment group was confirmed to be about $5.6\times10^8$ cells/ml, and the extracellular vesicles increased by $4.5\times10^8$ cells/ml. On the other hand, the amount of extracellular vesicles produced was found to be about $16.1\times10^8$ cells/ml in the treatment group in which lactoferrin 5 μg/ml+calcium composition was added to the serum replacement, and about $14\times10^8$ cells/ml increased, 1450% compared to the basal media. The amount of extracellular vesicles produced was about $17\times10^8$ cells/ml in the lactoferrin 10 μg/ml+calcium composition and was increased by 1590% compared to the basal media.

The above results show that the lactoferrin+calcium composition can increase the amount produced in proportion to the concentration through combination with a serum replacement.

Figure 5:
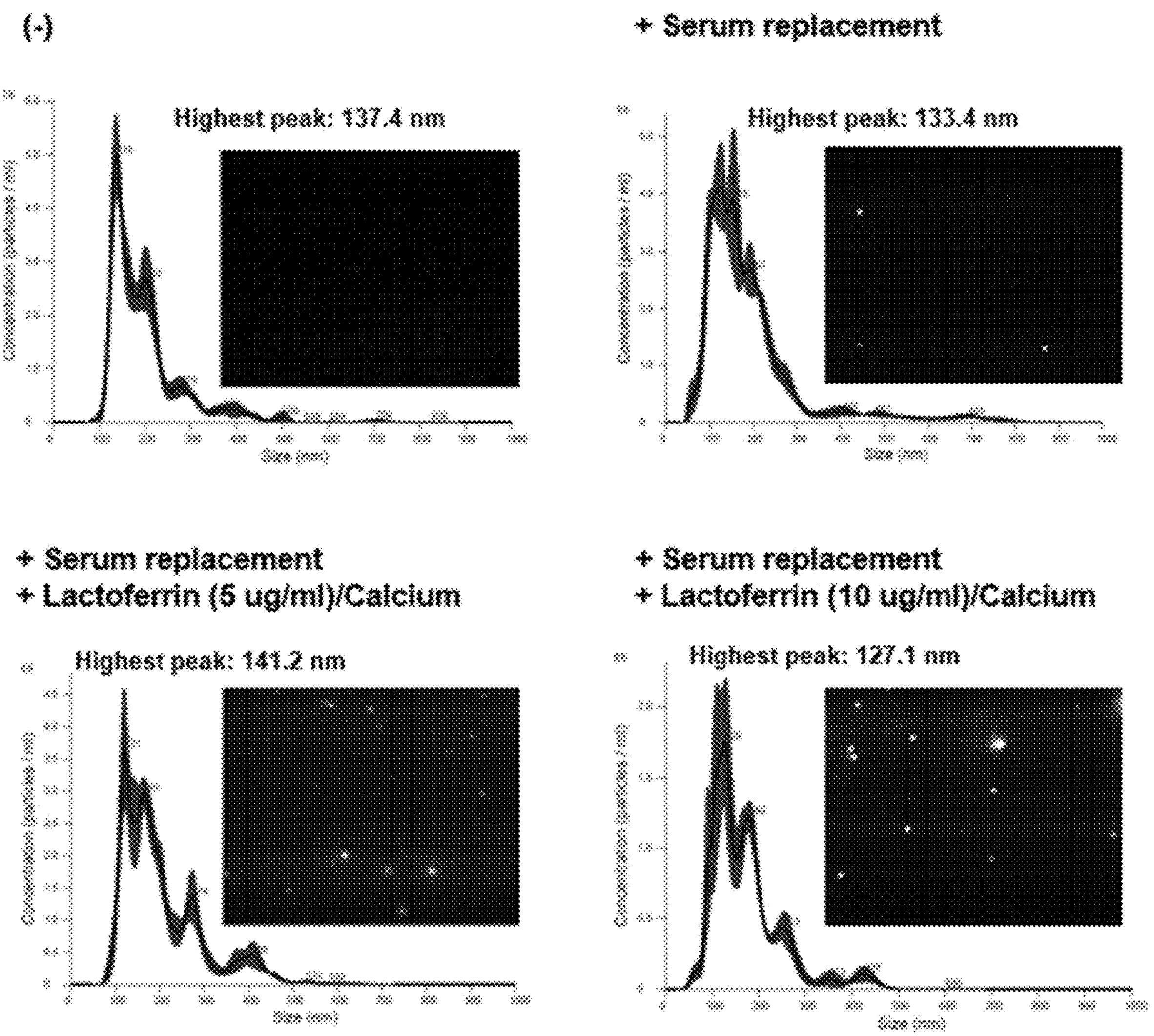
FIG. 5 is a result of confirming the size of extracellular vesicles generated in a conditioned medium with a nanoparticle tracking analyzer when a serum replacement, lactoferrin, and calcium are combined in the basal media.

On the other hand, as shown in FIG. 5, it was confirmed that the extracellular vesicles exist in a size range of 120 to 140 nm in the basal media treatment group, the serum replacement treatment group and the lactoferrin (5 or 10 μg/ml)+calcium composition treatment group. The image of the extracellular vesicle used in the size measurement is shown on the right side of the graph.

Example 4: Confirming that the Increase in Extracellular Vesicles by the Lactoferrin/Calcium Composition was Due to the Increase in Extracellular Vesicle Production Capacity of the Cells Serum replacements affect the production of extracellular vesicles by transferrin, but active metabolism due to nutrient supply increases cell proliferation, which increases the production of extracellular vesicles. An experiment was prepared to demonstrate that the lactoferrin+calcium composition clearly increases the productive capacity of extracellular vesicles expressed per cell, not the increase in cell proliferation or apoptotic substances.

Enzyme-linked immunoprecipitation assay (ELISA) was performed using CD9, a marker of extracellular vesicles, and calnexin, a marker of apoptotic vesicles, in order to observe the change in productive capacity of extracellular vesicles by the combination of lactoferrin and calcium.

Human adipose-derived mesenchymal stem cells were treated with the basal media (alpha-MEM), a medium containing a serum replacement, and a medium containing a serum replacement+10 μg/ml of lactoferrin+calcium. After 48 hours, the culture medium was centrifuged at 1500 g for 10 minutes, and then CD9 ELISA (exoquant overall exosome capture and quantification assay kit, Biovision, USA) and calnexin ELISA (calnexin ELISA kit, Mybiosource, USA) were performed as the supernatant.

The specific method of ELISA of CD9 is as follows. 100 μl of each standard and the obtained culture medium were added to the coated 96-well plate, and then reacted at 37° C. for 20 hours. Thereafter, the standard and the culture medium were removed and washed three times, and then the first antibody (detection antibody) was added and reacted at 37° C. After 2 hours, the mixture was washed 3 times with a washing buffer, and a second antibody (HRP antibody) was added thereto to react, and after 1 hour, the mixture was washed again. Finally, a substrate and a stop buffer were added, and the absorbance was measured at 450 nm with an ELISA reader (Molecular Devices, USA).

The measured values of calnexin and CD9 were divided by the proliferation rate (MTT assay) measured in cells when the culture medium was obtained. The MTT assay method is as follows. After removing the medium, the cells were washed three times with a phosphate buffer solution. The MTT reagent was diluted in a medium so that the treatment concentration was 0.5 mg/ml, followed by treatment and reacted at 37° C. for 2 hours. After washing with a phosphate buffer solution, the absorbance was measured at 570 nm by stirring for 30 minutes in 500 μl of isopropyl alcohol solution.

Figure 6:
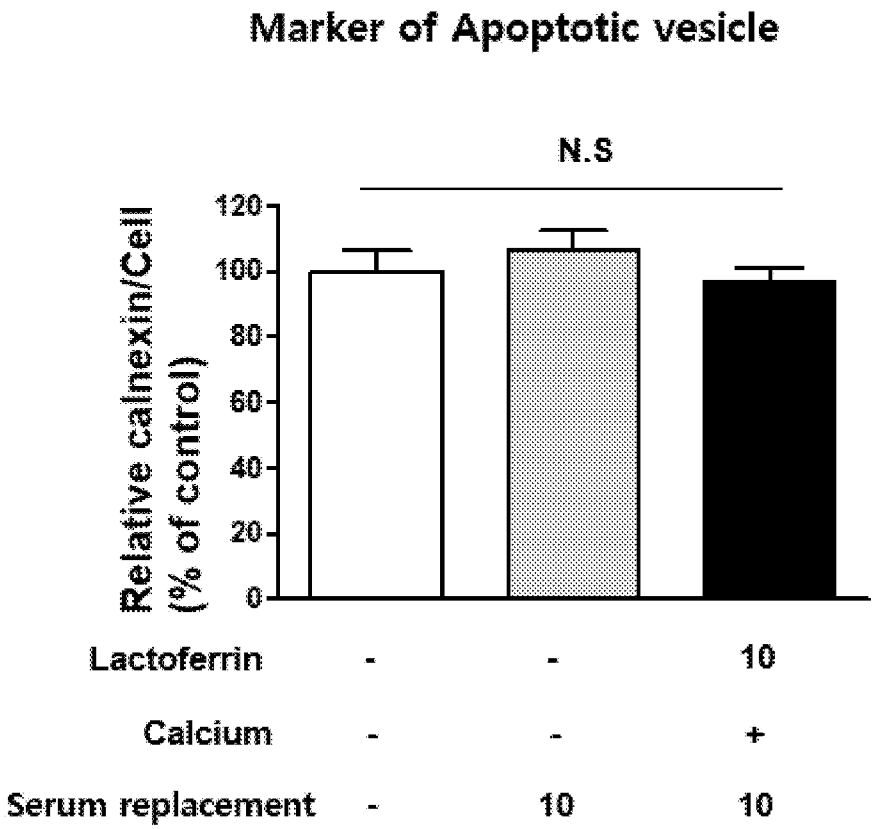
FIG. 6 is a calnexin ELISA result showing the relative amount of apoptotic vesicles produced by the same cells in the conditioned medium when the basal media alone, the serum replacement alone or the serum replacement+lactoferrin+calcium were combined.

The results of the apoptosis indicator are shown in FIG. 6 using 100% of the basal media. As shown in FIG. 6, the apoptosis factor was not specifically overexpressed in the produced extracellular vesicles. Overall, it was confirmed that the expression level of calnexin was similar in the basal media, the medium containing the serum replacement and the medium containing the serum replacement+lactoferrin+calcium composition (one-way ANOVA, $F(2, 3)=1.797$, $p>0.05$).

Figure 7:
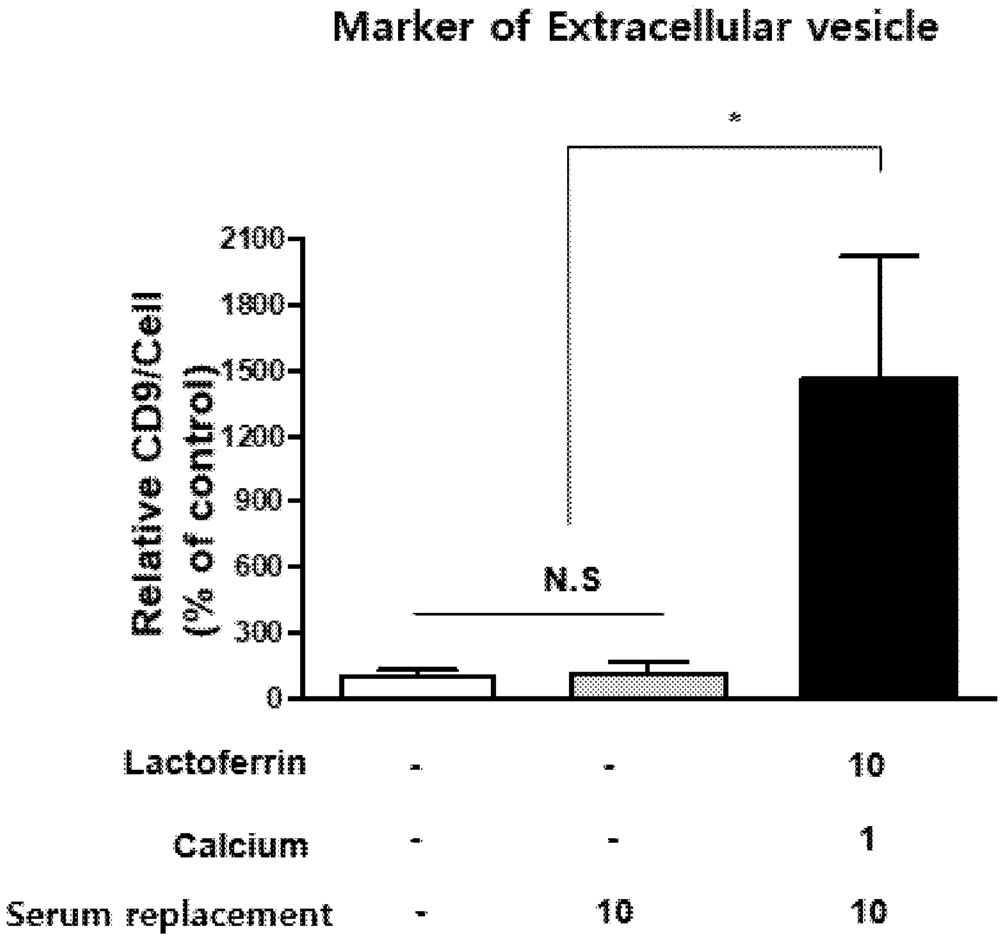
FIG. 7 is a CD9 ELISA result showing the relative amount of extracellular vesicles produced by the same cells in the conditioned medium when the basal media alone, the serum replacement alone or the serum replacement+lactoferrin+calcium were combined.

However, it was confirmed that CD9, a marker of extracellular vesicles, was significantly increased in the lactoferrin+calcium composition. It was confirmed that as shown in FIG. 7, since the medium containing the serum replacement using 100% of the basal media did not significantly increase the expression of CD9 per cell compared to the basal media, the effect of the serum replacement is the increase of the number of cells rather than the increase in the amount of extracellular vesicles produced per cell, and the production of extracellular vesicles increases (Tukey's test, $p>0.05$).

On the other hand, in the medium using the lactoferrin+calcium composition with a serum replacement, the CD9 expressed per cell increased by 1463% compared to the basal media, and results similar to the increase rate of extracellular vesicles (1590%) shown in Example 3 were confirmed. These results clearly demonstrate that the lactoferrin+calcium composition increased the productive capacity of extracellular vesicles produced by single cells (Tukey's test, $p<0.05$). In addition, the lactoferrin+calcium composition was identified as a composition that specifically increases the production amount of exosomes and microvesicles, which are two classifications of extracellular vesicles in the concentration range used.

It was confirmed by performing a one-way ANOVA that there was a difference within the entire group, and the difference between individual means was analyzed using Tukey's test. The statistical clarity between groups was plotted as *=($p<0.05$), N.S=($p>0.05$). The statistics were analyzed using Prism software version 5.

What is claimed is:

1. A method for increasing a productive capacity of extracellular vesicles produced per single cell comprising:
- culturing mesenchymal stem cells in a cell culture medium comprising lactoferrin and calcium,
  - wherein the cell culture medium comprises lactoferrin at a concentration of 2 μg/ml to 100 μg/ml,
  - wherein the cell culture medium comprises calcium at a concentration of 100 μM to 2 mM,
- harvesting the extracellular vesicles, and
  - wherein the method increases the productive capacity of extracellular vesicles produced per single cell in a manner than the number of extracellular vesicles in the cell culture medium obtained by culturing cells is in a range of $1.0\times10^8$/ml to $1.0\times10^{11}$/ml.

2. The method according to claim 1, wherein the use of the cell culture medium is not set at a specific time point during cell culture and is repeatedly used.

3. The method according to claim 1, wherein the lactoferrin is selected from the group consisting of holo-lactoferrin, apo-lactoferrin, and pis-lactoferrin.

4. The method according to claim 1, wherein the cell culture medium additionally comprises at least one substance selected from the group consisting of a basal medium, a serum replacement, and serum.

5. The method according to claim 1, wherein the cell culture medium is applied to cells derived from humans or animals.

* * * * *